(12) United States Patent
Goldstein

(10) Patent No.: US 7,195,018 B1
(45) Date of Patent: Mar. 27, 2007

(54) ADJUSTABLE SUPPORT SYSTEM FOR NASAL BREATHING DEVICES

(76) Inventor: Joseph Goldstein, 10560 Wilshire Blvd., #903, Los Angeles, CA (US) 90024

(*) Notice: Subject to any disclaimer, the term of this patent is extended or adjusted under 35 U.S.C. 154(b) by 0 days.

(21) Appl. No.: 11/136,804

(22) Filed: May 26, 2005

(51) Int. Cl.
*A61M 15/08* (2006.01)
*A61M 16/00* (2006.01)

(52) U.S. Cl. .................... 128/207.18; 128/200.24; 128/204.18; 128/207.14

(58) Field of Classification Search .......... 128/207.18, 128/207.17, 107.17, 200.29, 204.18, 207.14, 128/859, 862, 202.28, 205.25, 206.21, 848
See application file for complete search history.

(56) References Cited

U.S. PATENT DOCUMENTS

| 4,967,744 | A | * | 11/1990 | Chua | 128/204.18 |
| 5,752,510 | A | * | 5/1998 | Goldstein | 128/207.18 |
| 6,012,455 | A | * | 1/2000 | Goldstein | 128/207.18 |
| 2005/0072424 | A1 | * | 4/2005 | Kleen | 128/202.27 |

* cited by examiner

*Primary Examiner*—Justine R. Yu
*Assistant Examiner*—Shumaya Ali
(74) *Attorney, Agent, or Firm*—Allan M. Shapiro

(57) ABSTRACT

Two nasal breathing devices are supplied with continuous positive airway pressure for alleviation of sleep apnea. The two nasal breathing devices are each supported on a spiral flexible supply tube. The supply tubes pass through a block. The block is supported on the patient's head below his nostrils. A stop nut is threaded on each of the spiral flexible supply tubes. The supply tubes and nasal breathing devices are individually adjustable by rotating the stop nut on each of the supply tubes. In this way, the nasal breathing devices are individually adjusted for proper nasal contact and sealing.

9 Claims, 3 Drawing Sheets

ADJUSTABLE SUPPORT SYSTEM FOR NASAL BREATHING DEVICES

BACKGROUND OF THE INVENTION

Sleep apnea is a condition where breathing gets very shallow or stops while the patient is sleeping. Each pause in breathing typically lasts 20 seconds or more and can occur 20 or more times per hour. The most common type of sleep apnea is obstructive sleep apnea. During sleep, insufficient air can flow into the patient's lungs through his mouth or nose even though the patient is trying to breathe. When this happens, the blood oxygen content drops. Normal breathing starts again, usually with a snort or choking sound. Because of this phenomenon, the condition of sleep cannot pass through its normal stages. Therefore, restful, deep sleep is not achieved.

When a person is awake and normally during sleep, throat muscles keep the patient's throat open and air flows in and out of the patient's lungs. However, in obstructive sleep apnea, the throat closes during rest so the throat is partially or fully blocked. Breathing may become hard and noisy. Quite often, this is accompanied by snoring.

The delivery to the patient of continuous positive airway pressure, CPAP, to the patient often alleviates this condition. The increased airway pressure is sufficient to maintain the airway open when the patient inhales. Constant positive airway pressure is delivered to the patient from a blower. Masks are available, some of which cover just the nose, while others cover both the nose and mouth. Another method of delivering positive airway pressure to the patient is through the nostrils. Tubular nasal breathing devices are held against and sealed against the nostrils. These nasal breathing devices are supplied by the continuous positive airway pressure. The devices are supported on the head in the manner to provide proper support and sealing. This support may be by dental engagement or by head gear. The positioning of the nasal breathing devices and maintaining them in position so that they are sealed and comfortable is a continuing goal.

SUMMARY OF THE INVENTION

In order to aid in the understanding of this invention, it can be stated in essentially summary form that it is directed to an adjustable support system for positioning nasal breathing devices with respect to the nostrils so that continuous positive airway pressure can be supplied to the patient. The system includes a support block which is positioned with respect to the patient's nose and to two nasal breathing devices adjustably mounted on the support block to position them with respect to the patient's nose.

It is, thus, a purpose and advantage of this invention to provide an adjustable support system for nasal breathing devices wherein the two nasal breathing devices are independently adjustable for individual positioning.

It is another purpose and advantage of this invention to provide an adjustable support system for nasal breathing devices wherein each of the two nasal breathing devices is mounted on its own flexible supply tube and the supply tubes are individually adjustable with respect to a support block which is positioned with respect to the patient's head so that individual adjustability is achieved.

It is another purpose and advantage of this invention to provide an adjustable support system for nasal breathing devices which is convenient to adjust and maintain so that the patient can make the necessary adjustments for full utilization of the continuous positive airway pressure palliative effect.

The features of this invention which are believed to be novel are set forth with particularity in the appended claims. The present invention, both as its organization and manner of operation, together with further objects and advantages thereof, may be best understood by reference to the following description, taken in conjunction with the accompanying drawings.

DESCRIPTION OF THE PREFERRED EMBODIMENT

Figure 1:
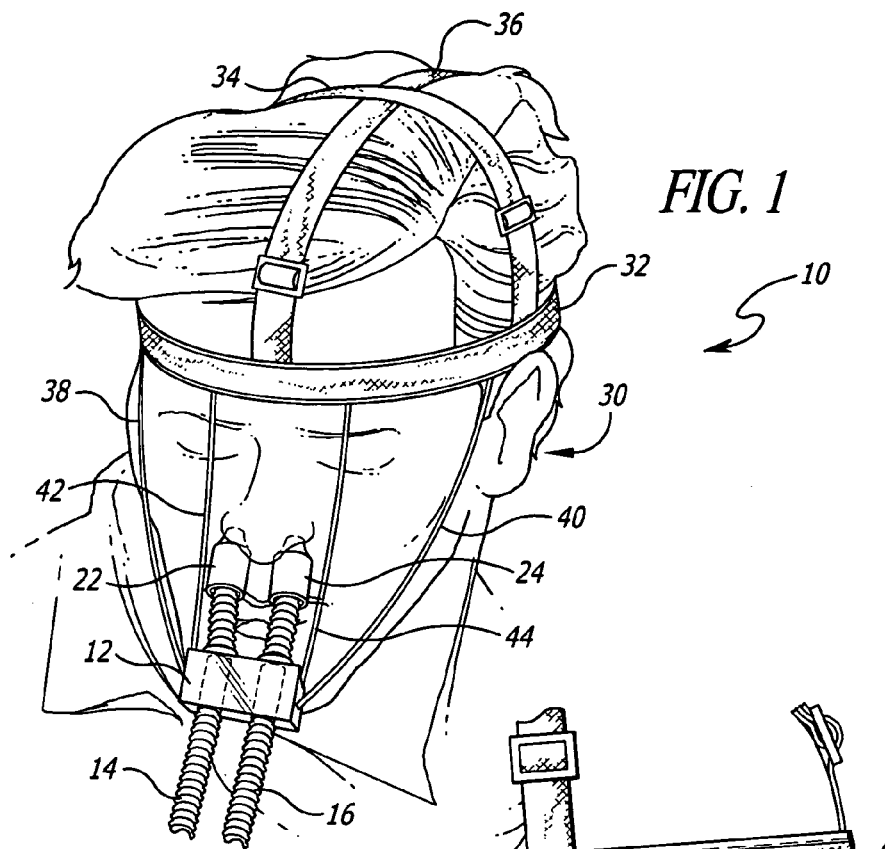
FIG. 1 is a perspective view of a patient wearing the adjustable support system for nasal breathing devices of this invention.
Figure 2:
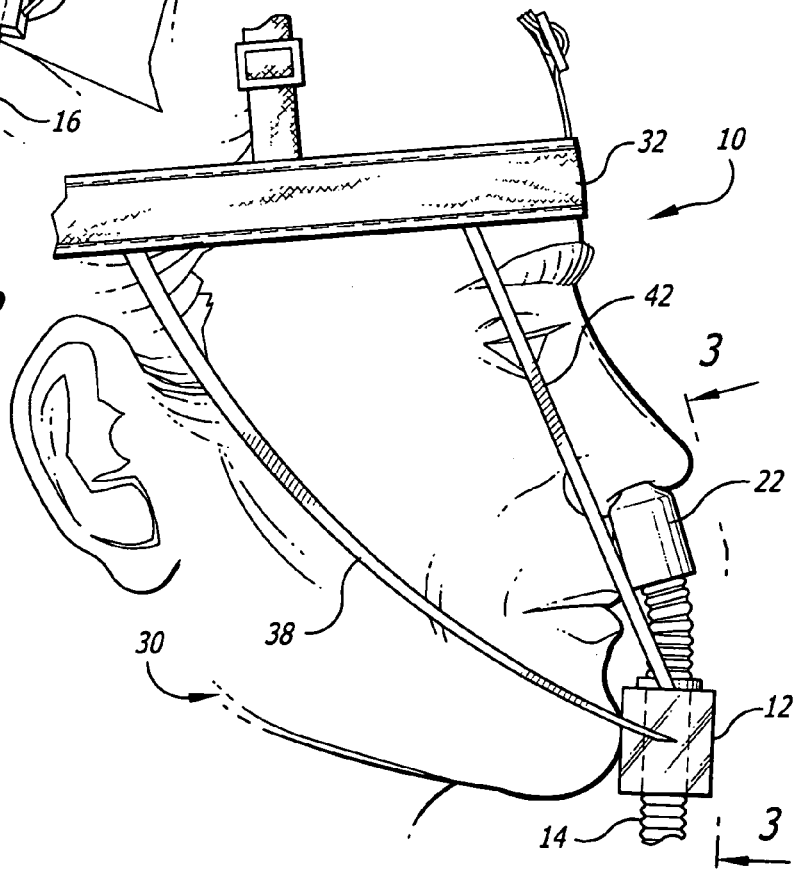
FIG. 2 is an enlarged side-elevational view thereof, with parts broken away.

The adjustable support system for nasal breathing devices is generally indicated at 10 in FIGS. 1 and 2. It comprises a block 12 through which first and second supply tubes 14 and 16 pass through clearance holes 18 and 20 (see FIG. 3). The top ends of the supply tubes 14 and 16 respectively carry first and second nasal breathing devices 22 and 24. The supply tubes 14 and 16 have a spiral exterior configuration, such as that manufactured by the teaching of U.S. Pat. No. 3,966,525. The tubes thus have a spiral exterior configuration which resembles a threaded configuration.

Stop nuts 26 and 28 have corresponding interior threaded configuration so that they rotatably engage upon the threads on the exterior of the supply tube. The stop nuts engage against the block 12, as seen with respect to the stop nut 28 in FIG. 3. When unengaged, the supply tube can be raised through the block for adjustment of the stop nut by rotation, as seen for nut 26 in FIG. 3. The supply tubes are free to move through the block and are limited in the downward direction by the stop nuts engaging on the top of the block.

The purpose of this construction is to place the nasal breathing devices at the nares of the patient 30. Thus, structure must be provided to maintain the block 12 in position below the patient's nose. In the example shown, an adjustable forehead strap 32 extends around the head of the patient at his forehead and above his ears. It is held upward by means of adjustable cross strap 34 and adjustable medial strap 36 (see FIG. 1). The ends of these straps are attached to the forehead strap 32 to hold it above the patient's ears. The block 12 is held up and back by means of cheek straps 38 and 40 and face straps 42 and 44. These four straps are attached at their upper ends to the forehead strap 32 and at their lower ends to the block 12. Adjustment of the straps 32, 34 and 36 places the block 12 below the patient's nose in a position where the supply tubes and nasal breathing devices can engage into the patient's nares. The straps 38, 40, 42 and 44 may also be adjustable.

The use of the head straps to support the block is an example of how the block can be placed in position. Other support structures can be used to support the block with respect to the patient's nose. The support structure must relate to the patient's head because the block must maintain a relationship with respect to the patient's nose. The block 12 is shown as being rectangular, but it is expected to be shaped in a manner to provide comfort if it is in contact with the patient and it is structured to be of light weight to be of minimum burden to the patient. Other supporting structures for the block with respect to the patient's nose are also possible.

Figure 3:
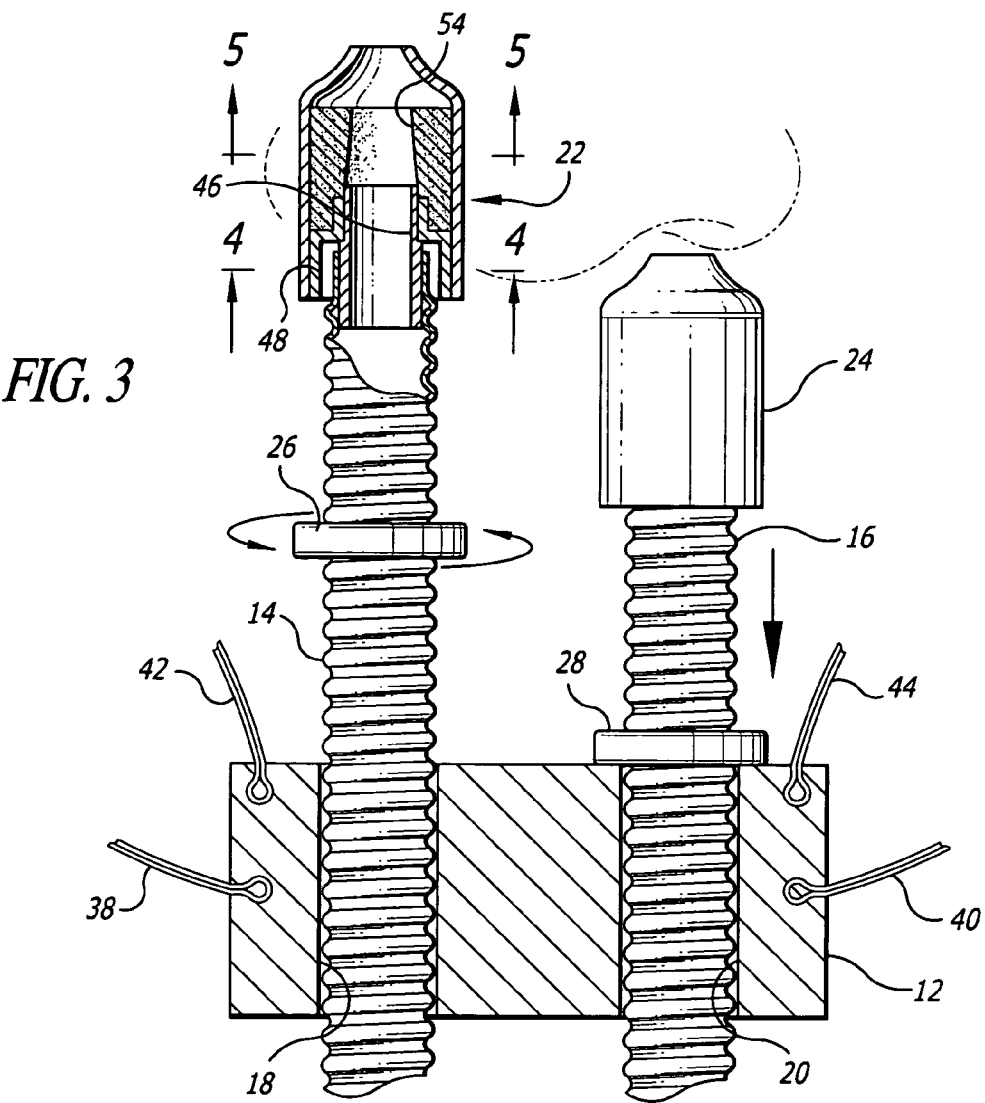
FIG. 3 is an enlarged front view, seen along the line 3—3 of FIG. 2, with parts broken away and parts taken in section.
Figure 4:
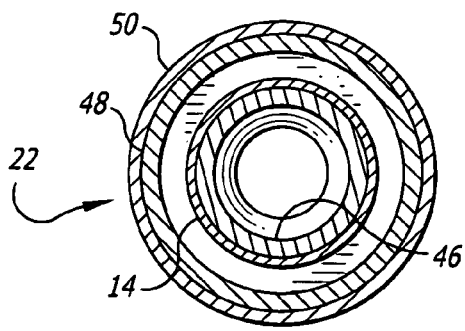
FIG. 4 is an enlarged section taken generally along the line 4—4 of FIG. 3.
Figure 5:
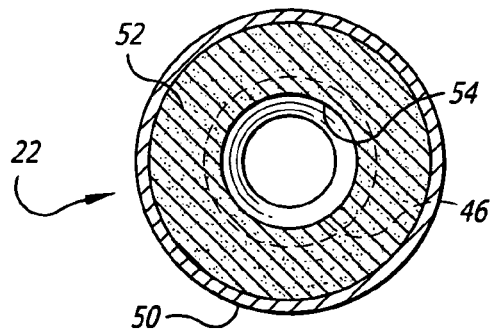
FIG. 5 is an enlarged section taken generally along line 5—5 of FIG. 3.
Figure 6:
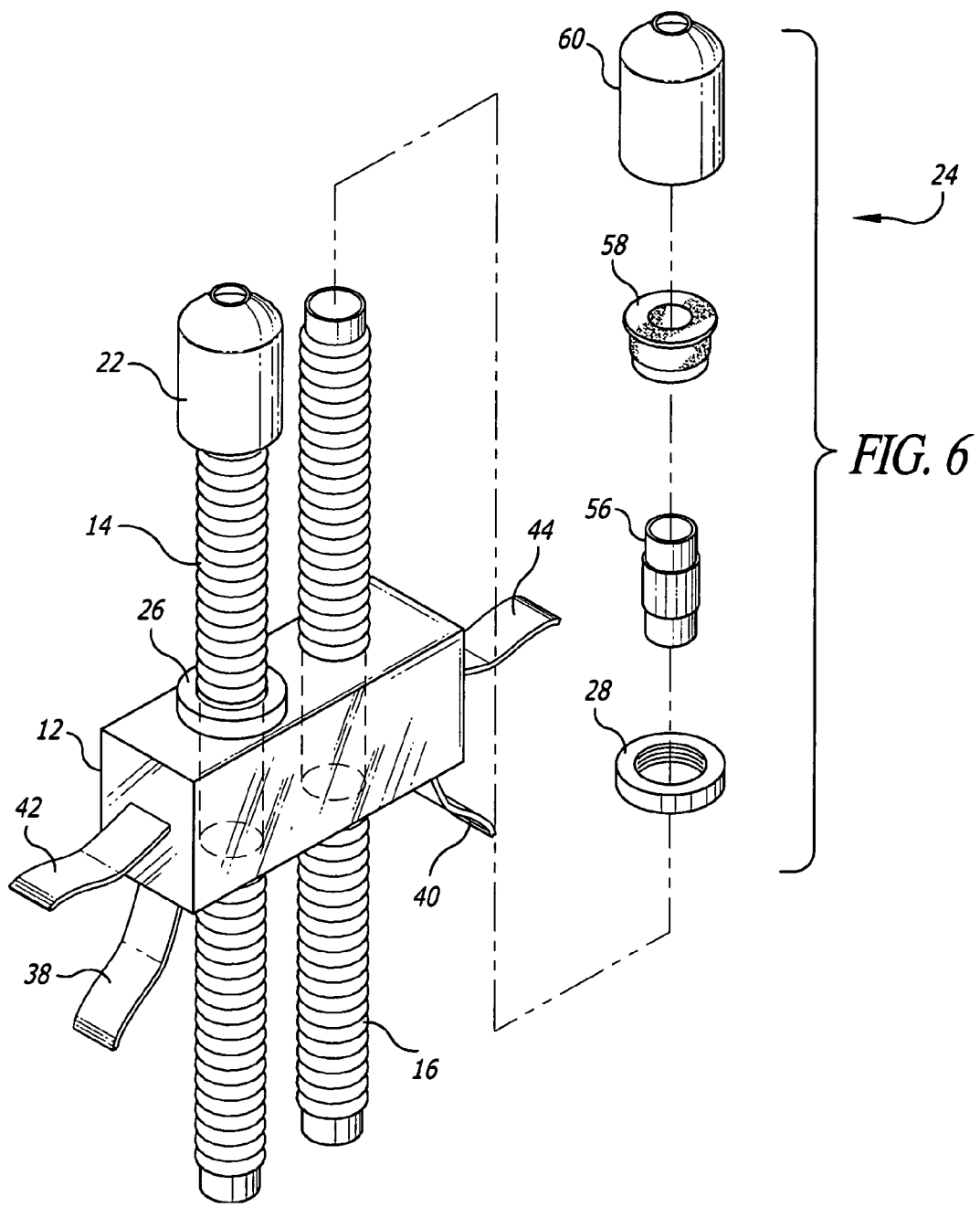
FIG. 6 is an exploded view of the adjustable support system for nasal breathing devices of this invention.

The nasal breathing devices 22 and 24 are examples of suitable nasal breathing devices for sealing into the nares. FIGS. 3, 4 and 5 show cross sections through nasal breathing device 22. FIG. 6 shows the exploded structure of nasal breathing device 24, which is identical to the nasal breathing device 22. As seen in FIGS. 3, 4 and 5, the nasal breathing device 22 comprises an attachment tube 46 which extends into the cylindrical tubular upper end of supply tube 14 above its threads. Adaptor tube 48 engages on the attachment tube and extends downward and outward with an enlarged skirt. Cover 50 is of soft, flexible material and attaches to the lower end skirt of the adaptor tube 48. The cover is filled with synthetic polymer foam 52, which tends to maintain the cylindrical external shape of the nasal breathing device. As seen in FIG. 3, the upper end of the cover narrows down to about the size of the opening 54 through the foam and through the attachment tube 46. This unsupported upper end of the cover is soft and flexible so as to readily achieve its seal in the nares of the patient. This structure is seen in the exploded position with respect to the nasal breathing device 24 shown in FIG. 6. FIG. 6 shows attachment tube 56, adaptor tube 58 and cover 60. This is an example of a suitable nasal breathing device. Other nasal breathing devices can be utilized.

In use, a source is connected to the lower ends of the supply tubes. In the case of continuous positive airway pressure systems, an air blower is used to provide air under constant pressure for the patient. The blower supplies air at a pressure which has been determined for the individual patient. Pressures up to about 0.25 psi are utilized. The block is positioned and supported beneath the patient's nasal structure. The supply tubes are individually thrust upward through the block into nasal engagement and, when suitable engagement is achieved, the stop nut is spun down the supply tube to engage against the top of the block. This holds the nasal breathing device sealed into the nares. The CPAP blower provides the pressure necessary to inflate the soft tissue in the patient's air passages to permit proper breathing and, thus, transition through the various progressive stages of sleep to achieve restful sleep.

The specific preferred embodiment illustrated is suitable for CPAP systems and is also suitable for the supply of other dispersions in air, such as might be delivered for other respiratory needs.

This invention has been described in its presently preferred embodiment, and it is clear that it is susceptible to numerous modifications, modes and embodiments within the ability of those skilled in the art and without the exercise of the inventive faculty.

What is claimed is:

1. An adjustable support system for nasal breathing devices, comprising:
   a support member at least one clearance hole through said support member, structure on said support member for supporting said support member with respect to the face of the patient;
   a flexible supply tube, a nasal breathing device on one end of said supply tube, said supply tube extending through said clearance hole in said support member, said flexible supply tube having a spirally configured exterior surface over at least part of its length,
   a stop nut having an interior threaded surface sized and configured to be threadedly engaged with said spiral exterior surface of said flexible supply tube so that said stop nut can be rotated with respect to said supply tube and move along the length of said supply tube as said nut is rotated, said nut engaging said support member to limit axial motion of said supply tube through said support member away from the patient's nares,
   so that said nasal breathing device can be adjusted with respect to the patient's nares by rotation of said stop nut on said spiral flexible supply tube to urge said nasal breathing device toward the patient's nares.

2. The adjustable support system for nasal breathing devices of claim 1 wherein there are first and second clearance holes through said support member and there are first and second flexible supply tubes each having a spirally configured exterior surface said first and second flexible supply tubes respectively extending through said first and second clearance holes in said support member and there are first and second stop nuts threadedly engaged respectively on said spiral external surfaces of first and second supply tubes and there are first and second nasal breathing devices respectively on said first and second flexible supply tubes.

3. The adjustable support system for nasal breathing devices of claim 2 wherein each said nasal breathing device includes an attachment tube for engagement with said flexible supply tube, and there is synthetic polymer foam over at least part of said attachment tube and a cover over said synthetic polymer foam, said cover having an opening therethrough open to said supply tube so that said nasal breathing device can seal with respect to the nares of the patient.

4. An adjustable support system for nasal breathing devices, comprising:
   a block, said block being for positioning with respect to a patient's face so that said block is below his nose;
   first and second supply tubes, each of said first and second supply tubes having an opening therethrough, each of said first and second supply tubes having an outlet end and inlet end, first and second nasal breathing devices respectively mounted on said outlet ends of said first and second supply tubes, each of said supply tubes having a spirally threaded exterior surface, said first and second supply tubes being movably mounted with respect to said block;
   first and second stop nuts respectively threadedly engaged on said spirally threaded exterior surface of said first and second supply tubes, said stop nuts being in engagement with said block to adjustably position said nasal breathing devices with respect to said block by limiting motion of said supply tubes away from the patient's nares.

5. The adjustable support system for nasal breathing devices of claim 4 wherein said block has a top surface and has first and second clearance holes through said block from said top surface, said first and second supply tubes respectively extending through said first and second clearance holes and said first and second nuts engaging on said top surface.

6. The adjustable support system for nasal breathing devices of claim 4 wherein there is structure attached to said block for supporting said block with respect to the patient's face.

7. The adjustable support system for nasal breathing devices of claim 6 wherein said block has a top surface and has first and second clearance holes through said block from said top surface, said first and second supply tubes respectively extending through said first and second clearance holes and said first and second nuts engaging on said top surface.

8. The adjustable support system for nasal breathing devices of claim 6 wherein said structure attached to said block for supporting said block with respect to the patient's face engages the patient's head.

9. The method of placing first and second nasal breathing devices at a patient's nares comprising the steps of:

provide first and second supply tubes respectively carrying the first and second nasal breathing devices and each having an externally spiral threaded surface, together with spiral threaded first and second stop nuts threadedly engaged on the first and second spiral threaded supply tubes;

positioning a block with respect to the patient's nasal structure and positioning the first and second externally spiral threaded supply tubes with respect to the block so that the stop nuts on the first and second spiral threaded supply tubes engage the block; and adjusting the first and second spiral threaded supply tubes with respect to the block and thus with respect to the patient's nares by rotating the first and second spiral threaded stop nuts on the first and second spiral threaded supply tubes to engage the nuts against the block to maintain the first and second spiral threaded supply tubes with the first and second nasal breathing devices in sealing engagement with the patient's nares.

* * * * *